United States Patent [19]
Larrick et al.

[11] Patent Number: 4,624,921
[45] Date of Patent: Nov. 25, 1986

[54] HUMAN LYMPHOBLASTOLD CELL LINE AND HYBRIDOMAS DERIVED THEREFROM

[75] Inventors: James W. Larrick, Woodside; Andrew R. Raubitschek, Palo Alto; Kenneth E. Truitt, San Diego, all of Calif.

[73] Assignee: Cetus Corporation, Emeryville, Calif.

[21] Appl. No.: 604,068

[22] Filed: Apr. 26, 1984

[51] Int. Cl.[4] .................. C12N 15/00; C12N 5/00; C12R 1/91
[52] U.S. Cl. .................. 435/172.2; 435/240; 435/948; 935/100
[58] Field of Search .................. 435/68, 172.2, 240, 435/241, 948; 935/100

[56] References Cited

U.S. PATENT DOCUMENTS 4,451,570 5/1984 Royston et al. .................. 435/948

FOREIGN PATENT DOCUMENTS 82301103 10/1982 European Pat. Off. .

OTHER PUBLICATIONS

Kozbor et al, "Human Hybridomas Constructed with Antigen-Specific Epstein-Barr Virus Transformed Cell Lines", Proceedings of the National Academy of Sciences, 79, pp. 6651–6655 (1982).

Physicians' Desk Reference, p. 1382, Litton Industries 31st Ed. (1977).

Choy et al, "Techniques for Using Hat Selection in Somatic Cell Genetics", Techniques in Somatic Cell Genetics, Ed. Shay, Plenum Press, NY, pp. 11–21 (1982).

Chiorazzi, N., et al., *J. Exp. Med.* (1982) 156:930–935.

Handley, H. H., et al, Proceedings of the 15th International Leucocyte Culture Conference, Asilomar (1982), p. 267.

*Primary Examiner*—Charles F. Warren
*Assistant Examiner*—John Edward Tarcza
*Attorney, Agent, or Firm*—Albert P. Halluin; Janet E. Hasak

[57] ABSTRACT

A 6-thioguanine-resistant subvariant of the EBV-transformed human lymphoblastoid B cell line WI-L2 is described. The subvariant line, designated LTR228, fuses efficiently with human cells. Human×human hybridomas derived from LTR228 that produce monoclonal antibodies against tetanus toxin and blood group A are exemplified.

8 Claims, No Drawings

HUMAN LYMPHOBLASTOLD CELL LINE AND HYBRIDOMAS DERIVED THEREFROM

DESCRIPTION

1. Technical Field

This invention is in the field of biotechnology and relates to somatic cell hybridization and immunochemistry. More particularly, it concerns a novel Epstein-Barr virus (EBV)-transformed human lymphoblastoid fusion partner, human×human hybridomas made with that lymphoblastoid line, and human monoclonal antibodies produced by those hybridomas.

2. Background Art

Kohler, B. and Milstein, C., *Nature* (1975) 256:495-497, pioneered the use of somatic cell hybridization to make continuous hybridomas that produce monoclonal antibodies. Their work used plasmacytomas and lymphocytes of murine origin. Subsequent investigators have reported applying Kohler and Milstein's techniques to human cells. Croce, C. M., et al, *Nature* (Lond) (1980) 288:488 and Olsson, L. and Kaplan, H. S., *PNAS* (USA) (1980) 77:5429.

Steinwitz, M., et al, *Nature* (1977) 269:420 and Luzzanti, A. G., et al, *Nature* (1977) 269:419 describe *in vitro* production of specific human antibodies from EBV-transformed human B lymphoblastoid cells. While the EBV transformation allowed these cells to be grown continuously, the cells typically lose their ability to secrete Ig in a short period of time. Several recent references describe using EBV-transformed human lymphoblastoid cell lines as parental tumor partners in fusions with Ig-producing human lymphocytes. European patent application No. 82301103.6 published 13 October 1982 describes such a line designated WI-L2-729 HF$_2$. This line is reported to be a hypoxanthine phosphoribosyl transferase (HPRT) deficient variant of the WI-L2 line (Levy, J. A., et al, *Cancer* (1968) 22:517). It is characterized as being nonsecreting, sIgMκ+, cyIgMκ+, and able to grow in serum-free media. Chiorazzi, N., et al, *J Exp Med* (1982) 156:930-935 describes another EBV-transformed human lymphoblastoid cell line derived from the WI-L2 line. This other line, designated H35.1.1, appears to have different characteristics than the WI-L2-729 HF$_2$ line. Handley, H. H., et al, Proceedings of the 15th International Leucocyte Culture Conference, Asilomar (1982), p. 267, describes an intermediate parent of the WI-L2-729 HF$_2$ line, designated UC729-6. UC 729-6 is reported to have characteristics common to WI-L2-729 HF$_2$ and was used as a fusion partner in making Ig-producing human×human hybridomas.

DISCLOSURE OF THE INVENTION

One aspect of the invention is the EBV-transformed human lymphoblastoid B cell line designated LTR228 and progeny of LTR228.

Another aspect of the invention relates to hybridomas of LTR228 and antibody-producing human cells and progeny of such hybridomas.

Another aspect of the invention is a method of making monoclonal antibody-producing human×human hybridomas comprising:

(a) fusing lymphoblastoid B cells of the line LTR228 with human antibody-producing cells in a fusion medium containing a fusogen;

(b) separating the cells from the fusion medium;

(c) expanding the separated cells; and (d) growing the expanded cells in a medium containing hypoxanthine and azaserine whereby said hybridomas are selected.

Still another aspect of the invention is a method of producing a human monoclonal antibody comprising:

(a) growing the above-described hybridoma in a growth medium; and (b) isolating human monoclonal antibody from the growth medium.

Another aspect of the invention is human monoclonal antibody SA13 and functional equivalents thereof.

Another aspect of the invention is hybridoma SA13 and progeny thereof.

Another aspect of the invention is a method for making human monoclonal antibody against tetanus comprising cultivating hybridoma SA13 in a growth medium and harvesting the antibody from the growth medium.

Another aspect of the invention is a pharmaceutical composition for treating tetanus comprising an effective amount of monoclonal antibody SA13 or a functional equivalent thereof admixed with a pharmaceutically acceptable parenteral vehicle.

Another aspect of the invention is a method of treating an individual for tetanus comprising administering an effective amount of monoclonal antibody SA13 or a functional equivalent thereof to the individual parenterally.

Modes for Carrying Out the Invention

As used herein with respect to the described cell lines the term "progeny" is intended to include all derivatives, issue, and offspring of cells of the described line regardless of generation or karyotypic identity. In this regard, it is well known that karyotypic changes may be induced or occur spontaneously depending upon the conditions under which the cells are maintained. In the case of the LTR228 line, progeny that possess the fusability, 6-thioguanine resistance, and growth characteristics of LTR228 are preferred.

As used herein the term "functional equivalent" means a human monoclonal antibody that recognizes the same determinant of tetanus as monoclonal antibody SA13 and crossblocks monoclonal antibody SA13. It is intended to include antibodies of the same or different immunoglobulin class and antigen binding fragments (e.g., Fab,F(ab)$_2$, Fv) of the monoclonal antibody.

As used herein with respect to the claimed antibodies the term "against" means that the antibody referred to recognizes and binds (in a noncovalent antigen-antibody reaction) specifically to the antigen referred to.

As used herein with respect to the administration of antibody to patients the term "treat" and conjugates thereof refers to therapy and/or prophylaxis.

The novel EBV-transformed human lymphoblastoid B cell line is a subvariant of the WI-L2 line. It was derived from a mycoplasma-contaminated generic WI-L2 parent by cloning the parent in soft agar, decontaminating the parent line, and culturing it in Iscove's medium containing 20 μg/ml 6-thioguanine (6-TG). LTR228 was selected from among the 6-TG resistant clones on the basis of its ability to fuse efficiently with normal B lymphocytes to produce stable human×human hybridomas. Fusion products of LTR228 plated at $10^5$ cells per microtiter plate well consistently show at least one colony per well.

LTR228 has a hyperdiploid modal chromosome number of 48. LTR228 cells are characterized by having: extra copies of chromosomes 13 and 20; a Robertsonian translocation between chromosomes 14 and 21; a copy of chromosome 8 with an enlarged short arm composed of a homogeneously staining region; and a marker 21 which has a translocation from the distal end of chromosome 11. LTR228's karyotype is: 48,XY,+13,+20,−14,+t(14q;21q),−21,−+der(21),t(11;21) (q13;p11),8pt+. LTR228 secretes small amounts of IgMκ and has a doubling time of about 16 hr. Its rapid growth rate and high cloning efficiency both in soft agar and by limiting dilution are important characteristics of the line.

LTR228 may be used as a parental tumor partner in fusions with a variety of other human cells. For making monoclonal antibody-producing hybrids it will be fused to Ig-producing human cells such as peripheral blood lymphocytes (PBLs), spleen cells, lymph node cells, bone marrow cells, and synovial tissue cells. PBLs are preferred because of their availability. The Ig-producing cells that are fused with LTR228 have been stimulated or sensitized by exposure to a target antigen to produce antibodies against the antigen. The target antigen may be an exogenous antigen or an autoantigen (i.e., an endogenous material that evokes an autoimmune response). The sensitized lymphocytes may be obtained from patients who have been infected naturally with the target antigen, immunized with the target antigen, or, in the case of autoantigens, from patients who suffer from autoimmune conditions. When in vivo inoculation with the target antigen is involved, the host is typically inoculated with the antigen and given one or more subsequent booster inoculations. Cells are usually collected from the host 2-3 weeks after the final booster.

Alternatively the cells may be sensitized in vitro by obtaining cells or tissue from the host, preparing a preparation of viable cells, if necessary, and culturing the cells in a nutrient medium that contains the target antigen at an appropriate concentration. When PBLs are used the nutrient medium will also contain macrophages. The cells will typically be incubated about 2-4 days in the antigen-containing medium.

The fusion procedure involves contacting parent cells in a fusogen-containing medium under conditions that promote formation of viable hybrids. The fusion medium typically comprises a balanced salt solution such as Hank's balanced salt solution containing polyethylene glycol (MW 1000-4000 daltons) at a concentration in the range of 30%-50%. The medium is preferably $Ca^{++}$ free and is at a pH of about 7.5-7.9. The medium optionally may contain additives such as dimethyl sulfoxide that promote efficient hybridization. The fusion may be carried out in the traditional "tube fusion" technique or by a plate technique in which the parent cells are adhered to the plate by means of a nontoxic binding agent such as peanut agglutinin. The ratio of LTR228 cells to the fusion partner will usually be in the range of about 10:1 to 1:10, more usually about 2:1 to 1:2. A cell ratio of 1:1 is preferred. The parent cells will typically remain in contact with the fusion medium for about 30 sec to two min. Thereafter the fusion mixture will be diluted by successive or continuous addition of balanced salt solution and then washed with balanced salt solution. After washing the cells are expanded in an appropriate growth medium and then seeded in microtiter plates containing a suitable selective medium such as enriched hypoxanthine-azaserine medium (Iscove's medium supplemented with 20% fetal calf serum, 14 μg/ml hypoxanthine, and 4 μg/ml azaserine). After culturing for about 10 to 20 days, unfused parent cells will have died, leaving the hybrids. The supernatants of the hybrids may be assayed for the presence of antibodies or other factors, as the case may be, by conventional immunoassay techniques such as radioimmunoassay or enzyme immunoassay. Desirable hybrids may be subcloned under limiting dilution conditions and single clones expanded to produce pure cultures of the desired hybridoma.

Hybridomas of LTR228 and antibody-producing fusion partners typically produce high titers of monoclonal antibody, usually between about 1 and 5 μg/ml of spent culture medium. The antibodies may be recovered from the culture medium by known techniques such as ammonium sulfate precipitation, diethylaminoethyl (DEAE) cellulose chromatography, affinity chromatography, electrophoresis, microfiltration and ultracentrifugation. Alternatively, the hybridomas may be grown in vivo by implanting them in a suitable mammalian host such as the nude mouse. Monoclonal antibodies may be recovered from the body fluids, e.g., ascites fluid, and serum, of the inoculated host after a sufficient inoculation period by the techniques mentioned above.

LTR228 may be made suitable for fusion with murine cells by making it resistant to ouabain. Ouabain resistance may be effected by culturing LTR228 cells in media containing increasing concentrations of ouabain. Ouabain-resistant progeny of LTR228 may be fused with either normal human cells or immortal (EBV-transformed) human cells or murine cells using the fusion protocol described above. The hybrid selection medium will, of course, be supplemented with ouabain.

The following examples describe fusions of LTR228 with various human cell populations. These examples are not intended to limit the invention in any manner.

Example 1: Fusion with PBLs

Prefusion Preparation of PBLs

White cells were isolated from human peripheral blood or spleen suspension on a ficoll-hypaque density gradient and washed twice in Hank's Balanced Saline Solution (HBSS). T cells were then removed by AET-SRBC rosetting (Madsen, M. and Johnson, H. E., *J Immun Methods* (1979) 27:61), irradiated (1500 rads), and recombined with the remaining lymphocytes in a 1 to 1 ratio. Mixed cells were cultured at a density of $10^6$/ml in Iscove's complete medium (ICM), 15% fetal calf serum (FCS), 1:100 pokeweed mitogen (PWM, Gibco) and harvested for fusion after three days.

Fusion Procedure

The fusion mixture contained polyethylene glycol (PEG) 4000, 40% (w/v); dimethylsulfoxide (DMSO), 10% (v/v) in HBSS−/+ ($Ca^{2+}$ free, 2 mM $MgSO_4$), supplemented with 5 μg/ml poly-L-arginine (Sigma, 70K–150K). Forty g of PEG 4000 were combined with 10 ml of DMSO and 50 ml of HBSS−/+. The mix was autoclaved for 25 min. When the solution had cooled to room temperature, poly-L-arginine from a filter sterilized 1000× stock solution was added to obtain a final concentration of 5 μg/ml. Before use, the pH of the fusion mixture was adjusted to 7.9 with sterile 0.1N NaOH. Fresh fusion mixture was made every two to three weeks.

Plates (Costar 3506, 6 well cluster, 35 mm well diameter) were prepared as follows: 2 ml of HBSS−/+ and 50 μl of a filter sterilized, 100 μg/ml, peanut agglutinin (PNA, Sigma) were added to each well. Plates were incubated at 37° C. for at least one hour prior to use. PNA stock was stored frozen, and a freshly thawed aliquot was used to coat fusion cells. Smaller sized wells were used if cell numbers were limited.

Cell populations were washed twice in HBSS−/+ at room temperature and subsequently resuspended and combined in HBSS−/+ warmed to 37° C. Two ml of the suspension (10–20 million cells) were added to each pretreated well containing PNA coating solution. Plates were spun at 400–500×g, room temperature, for six min to form a monolayer of cells. Supernatant was then aspirated off the plates.

Two ml of fusion mixture warmed to 37° C. were carefully added down the side of the fusion cell. After one min, the PEG solution was diluted with 37° C. 5% DMSO in HBSS−/+ (filter sterilized) at a rate of 2 ml/min (0.5 ml every 15 sec) for three min (6 ml). The fusion dilution mixture (FDM) was then added at a rate of 4 ml/min until the well was filled. FDM was always added down the side of the well, so as not to disturb the monolayer, and the plates were constantly swirled to ensure optimal mixing.

At this stage, the wells were aspirated. The remaining film of PEG mixture was diluted at a rate of 2 ml/min for two minutes with warm FDM. Again the plate was constantly swirled. Over a period of 15 sec, 5 ml of 37° C. HBSS−/+ were added to the fusion well, and all supernatant was aspirated from the monolayer. Finally, each fusion well was washed twice with 5–10 ml of warm HBSS−/+. Five ml of warm ICM, 15% FCS, were added to each well, and the plates were incubated at 37° C. for 18 hr. The cells were then removed from the wells by pipetting, spun down and resuspended in selective medium.

Hybrid Selection

Post-fusion cells were aliquotted into 96 well, flat bottomed, microtiter plates (Costar) at a density of $1-3 \times 10^5$/well. Enriched hypoxanthine-azaserine media (EHA) (Iscove's media supplemented with 20% FCS, 14 μg/ml hypoxanthine (Sigma) and 4 μg/ml azaserine (Sigma)) was used for hybrid selection. The "hybrid" nature of cells was confirmed via cell sorter generated DNA histograms. Hybrid colonies generally appeared 10–20 days post fusion.

Viability Staining

Hybrid formation was monitored with two fluorescent DNA-specific dyes. Hoescht 33258 (Calbiochem) stains the nuclei of both live and dead cells, while propidium iodide (Calbiochem) stains only the nuclei of cells with altered plasma membranes. As a result, "live" cells fluoresce blue, and "dead" cells fluoresce red. One can thus obtain a rough estimate of potentially viable hybrids by counting live cells with more than one nucleus within a few hours of fusion. An identical population of mixed, but not fused, cells served as a control.

Post-fusion cell samples were suspended in ICM, 15% FCS, and stained for 30 min with 5.0 μg/ml Hoescht 33258 and 20 μg/ml propidium iodide. Samples were then cytofuged onto slides and visualized under a fluorescence microscope. The table below shows the results of these tests.

| Number LTR228 Cells | B Cell Partner Population | Number Partner Cells | Plating Density | Percent Wells With Positive Growth |
| --- | --- | --- | --- | --- |
| $1.5 \times 10^7$ | PBL | $1.5 \times 10^7$ | $1.5 \times 10^5$/well | 26 |
| $6.1 \times 10^6$ | PBL | $6.1 \times 10^6$ | $1.3 \times 10^5$/well | 27 |
| $1.5 \times 10^7$ | PBL | $1.5 \times 10^7$ | $1 \times 10^5$/well | 50 |
| $2.5 \times 10^7$ | PBL | $2.5 \times 10^7$ | $1 \times 10^5$/well | 32 |
| $1.8 \times 10^7$ | Spleen | $1.8 \times 10^7$ | $2.0 \times 10^5$/well | 95 |
| $1.8 \times 10^7$ | Spleen | $3.6 \times 10^7$ | $2.9 \times 10^5$/well | 72 |

Example 2: Preparation of Monoclonal Anti-tetanus Antibody-producing Hybridoma Patient JB was vaccinated intramuscularly with tetanus toxoid (TT) (Wyeth Labs). Eighty ml of peripheral blood was obtained on day 9 post-vaccination and B cells were prepared therefrom for fusion, fused with LTR228, and hybrids selected from the fusion mixture as in Example 1.

Supernatants from cultures were tested for anti-TT antibody and total immunoglobulin by the enzyme-linked immunosorbent assay (ELISA) (Engvall, E. and Perlmann, P., G Immunochemistry (1971) 8:871) as follows.

Tetanus ELISA

Microtiter wells (Costar) were coated with purified TT (Massachusetts State Labs) at a concentration of 10 μg/ml in sodium carbonate buffer (50 mM pH 9.5) at 4° C. overnight. Wells were blocked with 1% BSA and 0.1% gelatin in PBS for 2 hours at 37° C. Culture supernatants and anti-tetanus containing human serum standards were diluted in PBS and incubated for 1 hr at 37° C. Wells were washed with PBS and developed with peroxidase conjugated goat anti-human, $\kappa, \lambda, \mu$, or $\gamma$, chain specific antibodies (diluted 1:1000 in PBS-BSA/gelatin) (DAKO Labs, Accurate Chemicals, Westburg, NY). After a final wash, step substrate ABTS (2,2'-azino-di(3-ethylbenzthiazoline sulphonic acid)) was added and $OD_{415}$ was read in a titertek ELISA plate reader (Flow Labs, Bethesda, MD).

Immunoglobulin ELISA

The immunoglobulin levels of culture supernatants were measured by a specific inhibition ELISA. Wells were coated with purified human immunoglobulin (10 μg/ml, pH 9.5 carbonate buffer) at 4° C. overnight. Wells were blocked as above. Supernatants or standards and affinity purified peroxidase-labeled anti-$\kappa$, $\lambda, \mu$, or $\gamma$ were mixed and added to the wells. The plates were washed and the assay was developed in a manner identical to the tetanus ELISA.

General Biochemical Methods

For internal labeling, $20 \times 10^6$ cells were incubated in 4 ml of methionine-free media with 1% (dialyzed) FCS and $35_S$-methionine (0.8 mCi) (New England Nuclear) overnight. Culture supernatants were immunoprecipitated with chain specific rabbit anti-human antibodies (DAKO) attached to staphylococcal A-containing bacteria. Immunoprecipitates were electrophoresed on a 5%–15% polyacrylamide gradient gel in sodium dodecyl sulfate (SDS). Gels were stained in Coumassie blue, prepared for fluorography by an hour soak in En³ance ™ (New England, Nuclear) and dried. Dupont Cronex film was used for fluorography.

Monoclonal anti-tetanus antibody was purified by Staph-protein A-sepharose affinity chromatography (Pharmacia Fine Chemicals, Uppsala, Sweden). Antibody was eluted by pH 2.3 100 mM acetate buffered 150 mM NaCl.

Every well produced growing hybridomas giving a hybridization frequency of at least 1 per $1.3 \times 10^5$ cells. Almost half of the wells produced immunoglobulin of the IgG and/or the IgM class. Five wells were strongly positive by tetanus ELISA. These wells were cloned by limiting dilution and in soft agar. One clone, designated E1, was selected for further in depth characterization. This line was cloned a second time by limiting dilution, by EPICS V cell sorter and in soft agar. E1 doubles every 25 to 28 hr and can be easily adapted to growth in serum-less media supplemented with bovine serum albumin (BSA) (700 μg/ml), transferrin (10 μg/ml) and insulin (0.2 unit/ml). Under these conditions, the time required for cultures to reach confluence is 30% longer than in Iscove's DMEM with 15% FCS. E1 clones have exhibited a stable tetraploid DNA content and the ability to maintain antibody secretion over prolonged periods and despite significant expansion. Selected E1 clones are capable of producing up to 10 μg antibody per ml spent culture medium. The antibody secreted by E1 is an IgG, κ-specific for tetanus toxin. This cell line and the antibody produced by it were designated SA13.

SA13 has been adapted to growth in nude mice. Inoculation of $10^7$ cells subcutaneously produces tumors within 3-4 weeks. After removal from the mouse and subsequent in vitro culture, this clone has permitted the production of ascites with a high titer of human monoclonal antibody. When nude mice were injected with adapted cells ($2 \times 10^7$), ascites containing 0.5 mg of specific antibody per ml formed within 2 weeks.

Outbred Swiss-Webster mice (20 g) were injected intraperitoneally (0.5 ml) with various doses of tetanus toxin mixed with serum-free medium conditioned by either SA13 hybridoma or LTR228 cells. Doses of toxin were 1-1000 times the $LD_{50}$. Results in the table below show that the monoclonal antibody is protective in vivo against the lethal effects of tetanus toxin.

| Toxin units* | Medium | |
|---|---|---|
| | Parent cell line | Antitetanus hybrid |
| 0 | 3/3 | 3/3 |
| 1 | 1/2 | 3/3 |
| 10 | 0/3 | 3/3 |
| 100 | 0/3 | 3/3 |
| 1000 | 0/3 | 2/3 |

Results indicate surviving mice (at day 4)/total mice injected.
*1 unit = $LD_{50}$.
+0.5 ml of spent medium was mixed with tetanus toxin and injected intraperitoneally.

The above described tests indicate that the monoclonal antibody is effective for treating tetanus in mammals, including humans. Accordingly, the antibody or functional equivalents of it may be used to passively immunize individuals who suffer from tetanus or are at risk with respect to tetanus infection. In such treatment the antibody will normally be administered parenterally (e.g., intravenously, intraarterially, intramuscularly, intraperitoneally), preferably intramuscularly. The dose and dosage regimen will depend upon whether the antibody is being administered for therapeutic or prophylactic purposes, the patient, and the patient's history. In the case of adult humans an injection of 250-500 units of the antibody intramuscularly will typically provide protection for 2-4 weeks (a unit of antitoxin is the activity contained in 0.03384 mg of the Second International Standard for Tetanus Antitoxin). For therapy, larger doses in the range of 3,000-10,000 units will typically be administered. For therapeutic treatment of neonatal tetanus lesser doses in the range of about 200-500 units will be administered. Such doses are examples of "effective" amounts of the antibody.

For parenteral administration the antibody will be formulated in a unit dosage injectable form (solution, suspension, emulsion) in association with a pharmaceutically acceptable parenteral vehicle. Such vehicles are inherently nontoxic and nontherapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The antibody will typically be formulated in such vehicles at concentrations of about 1 mg/ml to 10 mg/ml.

Example 3: Preparation of Hybridoma that Produces an Anti-blood Group A Antibody LTR228 cells were made resistant to ouabain by culturing them in ICM containing $10^{-8}$M ouabain. Resistant cells were expanded and the concentration of ouabain was increased gradually. The procedure was repeated until the cells could survive $10^{-6}$M ouabain. Clones were selected from soft agar supplemented with 6-TG (20 μg/ml) and ouabain ($10^{-6}$M).

White cells were isolated from a sample of spleen cells of a child with thalassemia as in Example 1. These cells were rosetted by treatment with papain and A group red blood cells (ARBC) (Pap/ARBC). Rosetting cells were separated by ficoll-hypaque gradient centrifugation and EBV-transformed with 10% marmoset B-958 soup. The transformed cells were plated on a 96 well Costar plate at $4 \times 10^5$ cells/well.

Anti-A Ig containing wells were identified by an ARBC agglutination test. Two positive wells were identified, but only one, designated E6, survived. E6 cells were enriched by rosetting with Pap/ARBC and gradient centrifugation (yield ~10%) and then cloned in soft agar. Colonies were picked, expanded and assayed for anti-A activity by ARBC agglutination. One subclone, identified as E6C6, was chosen for fusion with ouabain-resistant LTR228 and expanded.

Ouabain-resistant LTR228 and E6C6 were fused at a 1:1 cell ratio using the fusion procedure of Example 1. The day following fusion the cells were plated at $10^5$ cells/well in ICM containing azaserine (2 μg/ml) and ouabain ($10^{-6}$M). Growing hybrids were visible by day 10 and growing wells were tested for anti-A activity by hemagglutination on day 21. Positive wells were recloned in soft agar.

Samples of LTR228 and the hybridomas of Examples 2 and 3 were deposited at the American Type Culture Collection, 12301 Parklawn Dr., Rockville, Md. Deposit dates and accession numbers are listed below.

| Ex. No. | Cell Line Designation | Deposit Date | Accession Number |
|---|---|---|---|
| 2 | LTR228 TG | 14 February 1984 | HB8502 |
| | SA13 | 14 February 1984 | HB8501 |

| Ex. No. | Cell Line Designation | Deposit Date | Accession Number |
|---|---|---|---|
| 3 | HAA1 | 28 March 1984 | HB8534 |

The above identified deposits were made under the Budapest Treaty and will be maintained and made available in accordance with the provisions thereof.

Using obvious variations of the above-described procedures, LTR228 may be fused with other human antibody-producing cells to make hybridomas that secrete monoclonal antibodies against any hapten or antigen, including various drugs, cell surface antigens, toxins, and the like. Monoclonal antibodies produced by hybrids of LTR228 may find use in therapy, diagnostics, or chromatography.

We claim:

1. A human lymphoblastoid B cell of the line LTR228 and progeny thereof.

2. A ouabain-resistant progeny of the lymphoblastoid B cell of claim 1.

3. A monoclonal antibody-producing human×human hybridoma of:
    (a) a human lymphoblastoid B cell of the line LTR228 or a progeny thereof; and
    (b) an antibody-producing human cell.

4. The hybridoma of claim 3 wherein the monoclonal antibody is an anti-tetanus toxoid antibody.

5. A method of producing a human monoclonal antibody comprising:
    (a) growing the hybridoma of claim 3 in a growth medium; and
    (b) isolating human monoclonal antibody from the growth medium.

6. A method of making monoclonal antibody-producing human×human hybridomas comprising:
    (a) fusing lymphoblastoid B cells of the line LTR228 or progeny thereof with human antibody-producing cells in a fusion medium containing a fusogen;
    (b) separating the cells from the fusion medium;
    (c) expanding the separated cells; and
    (d) growing the expanded cells in a medium containing hypoxanthine and azaserine and lacking thymidine whereby said hybridomas are selected.

7. Human×human hybridoma SA13 and progeny thereof.

8. A method for making monoclonal antibody SA13 comprising cultivating hybridoma SA13 in a growth medium and harvesting the antibody from the growth medium.

* * * * *

UNITED STATES PATENT AND TRADEMARK OFFICE
CERTIFICATE OF CORRECTION

PATENT NO.   :   4,624,921

DATED        :   November 25, 1986

INVENTOR(S)  :   James W. Larrick et al

It is certified that error appears in the above-identified patent and that said Letters Patent is hereby corrected as shown below:

Title page, item [54]
        and
Column 1, line 1, change "LYMPHOBLASTOLD" to --LYMPHOBLASTOID--.

Signed and Sealed this

Twenty-third Day of August, 1988

Attest:

DONALD J. QUIGG

Attesting Officer      Commissioner of Patents and Trademarks